US00PP29323P3

(12) United States Plant Patent
Bergman

(10) Patent No.: US PP29,323 P3
(45) Date of Patent: May 29, 2018

(54) ***MANDEVILLA* PLANT NAMED 'MANZ0003'**

(50) Latin Name: ***Mandevilla sanderi* (Hemsl.) Woodson**
Varietal Denomination: MANZ0003

(71) Applicant: SYNGENTA PARTICIPATIONS AG, Basel (CH)

(72) Inventor: Wendy R. Bergman, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 19 days.

(21) Appl. No.: 14/999,840

(22) Filed: Jul. 7, 2016

(65) Prior Publication Data

US 2018/0014446 P1 Jan. 11, 2018

(51) Int. Cl.
*A01H 5/02* (2018.01)

(52) U.S. Cl.
USPC ..... Plt./232
CPC ..... *A01H 5/02* (2013.01)

(58) Field of Classification Search
USPC ..... Plt./232
See application file for complete search history.

(56) References Cited

PUBLICATIONS

UPOV hit on *Mandevilla* plant named 'Manz0003', CA PBR 15-8599, filed Apr. 10, 2015.*

* cited by examiner

*Primary Examiner* — Anne Marie Grunberg
(74) *Attorney, Agent, or Firm* — Dale Skalla

(57) ABSTRACT

A new *Mandevilla* plant named 'MANZ0003' particularly distinguished by its large lavender pink flowers, glossy and smooth medium green foliage, bushy plant habit with a tendency to produce vines under low light growing conditions and with excellent branching and floriferousness.

1 Drawing Sheet

Latin name of the genus and species of the plant claimed: *Mandevilla sanderi* (Hemsl.) Woodson.

Varietal denomination: 'MANZ0003'.

BACKGROUND OF THE NEW PLANT

The present invention comprises a new *Mandevilla*, botanically known as *Mandevilla sanderi*, and hereinafter referred to by the variety name 'MANZ0003'.

'MANZ0003' is a product of a planned breeding program. The new cultivar has large light lavender pink flowers, glossy and smooth medium green foliage, bushy plant habit with a tendency to produce vines under low light growing conditions and with excellent branching and flower production.

'MANZ0003' originates from a hybridization made in a controlled breeding program in Hillscheid, Germany. The pollinations were made in 2007.

The female parent was an unpatented, proprietary plant identified as 'Rio White' ('K05-2007-1') and having white flower color and large flower size.

The male parent of 'MANZ0003' was an unpatented, proprietary plant identified as 'K04-1263-32' with red flower color and a vining habit.

The resulting seeds were sown in March 2010 and 'MANZ0003' was selected as one flowering plant within the progeny of the stated cross in December 2010 in a greenhouse in Gilroy, Calif.

The first act of asexual reproduction of 'MANZ0003' was accomplished when vegetative cuttings were propagated from the initial selection in January 2011 in a controlled environment in Gilroy, Calif.

BRIEF SUMMARY OF INVENTION

Horticultural examination of plants grown from cuttings of the plant initiated in May 2011 in Gilroy, Calif., and continuing thereafter, has demonstrated that the combination of characteristics as herein disclosed for 'MANZ0003' are firmly fixed and are retained through successive generations of asexual reproduction.

'MANZ0003' has not been observed under all possible environmental conditions. The phenotype may vary significantly with variations in environment such as temperature, light intensity and day length.

A Plant Breeder's Right for this cultivar was applied for in Canada on Apr. 10, 2015 and assigned No. 15-8599. 'MANZ0003' has not been made publicly available prior to the effective filing date of this application, notwithstanding any disclosure that may have been made less than one year prior to the effective filing date of this application by the inventor or another who obtained 'MANZ0003' directly from the inventor.

The following traits have been repeatedly observed and are determined to be basic characteristics of the new variety. The combination of these characteristics distinguishes this *Mandevilla* as a new and distinct variety.

BRIEF DESCRIPTION OF THE PHOTOGRAPHS

The accompanying photographic drawings show typical flower and foliage characteristics of 'MANZ0003' with colors being as true as possible with an illustration of this type.

Figure 1:
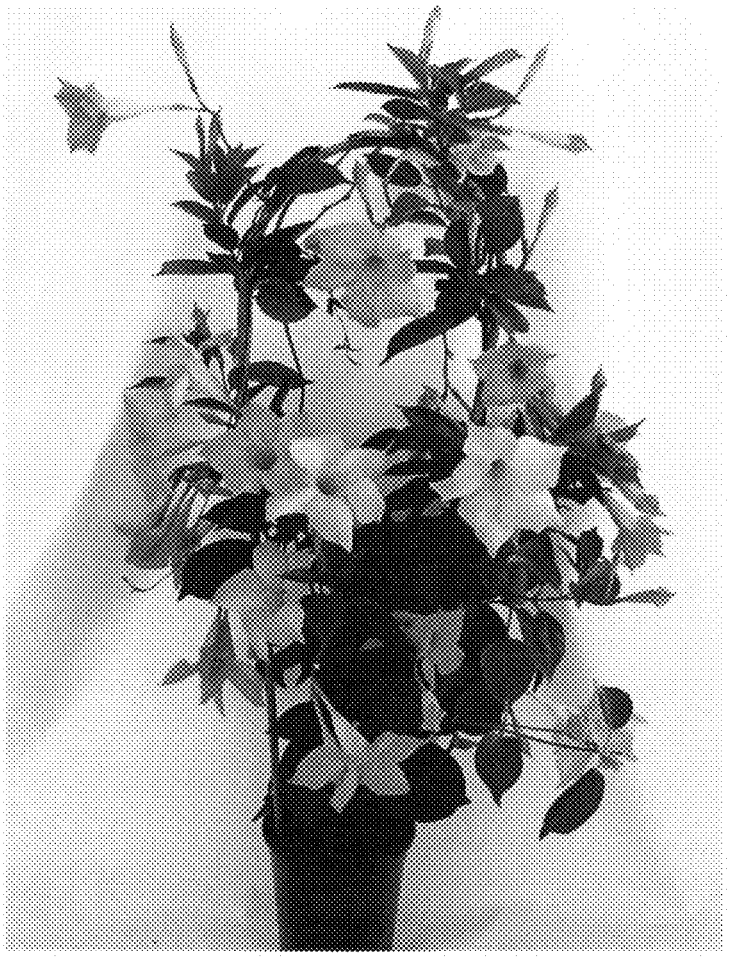
Figure 2:
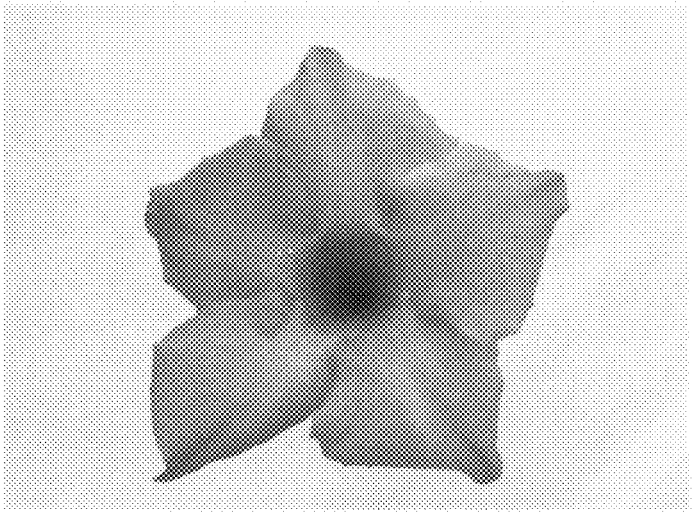

The photographic drawings show in FIG. 1, a flowering potted plant of the new variety and in FIG. 2, a close-up of the flowers.

DETAILED BOTANICAL DESCRIPTION

The aforementioned photographs were taken June 2016 in Gilroy, Calif. The plants were growing in 11 cm pots on benches in a greenhouse. They were about 5 months in age.

TABLE 1

DIFFERENCES BETWEEN THE NEW VARIETY 'MANZ0003' AND A SIMILAR VARIETY

| | 'MANZ0003' | 'FISRIX PINKA' ('Rio Pink' U.S. Plant Pat. No. 20,644) |
|---|---|---|
| Flower size: | Larger | Smaller |
| Flower color: | Lighter pink | Darker pink |
| Foliage: | Larger | Smaller |
| Plant size or habit: | Larger, more vigorous | Smaller, less vigorous |

Plant:

*Form, growth and habit.*—Perennial or sub-shrub, herbaceous younger stems, woody at base of older stems, spreading, semi-upright, with moderate tendency of developing vines depending on season and light intensity. Time for producing a commercial, flowering plant approximately is 12 weeks for one plant in a quart size container.

*Plant height.*—50 cm.

*Plant height (inflorescence included).*—52 cm.

*Plant width.*—37 cm.

Roots:

*Number of days to initiate roots.*—About 16-20 days at about 22 degrees C.

*Number of days to produce a rooted cutting plant.*—5 weeks at about 22 degrees C.

*Type.*—Fibrous, a little fleshy, free branching.

*Color.*—RHS N155D.

Foliage:

*Arrangement of leaves.*—Simple leaf, opposite and decussate.

*Immature leaf, color upper surface.*—RHS 137A.

*Immature leaf, color lower surface.*—RHS 146C.

*Mature leaf, color upper surface.*—RHS 139A.

*Mature leaf, color lower surface.*—RHS 137C.

*Length.*—9.0-9.5 cm.

*Width.*—5.3-6.3 cm.

*Shape.*—Ovate.

*Base shape.*—Rounded.

*Apex shape.*—Cuspidate.

*Margin.*—Entire.

*Texture, upper surface.*—Smooth, glossy, glabrous.

*Texture, lower surface.*—Smooth, glossy, glabrous.

*Pattern of leaf veins.*—Pinnate.

*Color of veins, upper surface.*—RHS 143D.

*Color of vein (midrib), lower surface.*—RHS 141D.

*Petiole color.*—RHS 141D.

*Length.*—0.8-1.6 cm.

*Diameter.*—0.25 cm.

*Petiole, texture.*—Glabrous.

Stem:

*Branching characteristics.*—Moderately free branching.

*Quantity of main branches per plant.*—3-5.

*Color of stem.*—RHS 144B with some anthocyanin present.

*Length of stem.*—70-90 cm.

*Diameter (at about mid point).*—0.3 cm.

*Length of internodes.*—3.0-21.0 cm.

*Stem, texture.*—Smooth and glabrous.

Inflorescence:

*Type of inflorescence.*—Raceme of several flowers, emerging from nodes of the stem.

*Number of flowers per inflorescence.*—4-11.

*Blooming habit.*—Continuously through the summer months.

*Quantity of flowers per plant.*—About 30 in various stages of development.

*Lastingness of individual blooms on the plant.*—Approximately 8-10 days, depending on temperature.

*Fragrance.*—Absent.

Peduncle:

*Color.*—Green, RHS 144A.

*Length.*—7.0-15.0 cm.

*Diameter.*—0.2 cm.

*Texture.*—Smooth, glabrous, somewhat glossy.

Bud (just before opening/showing color):

*Color.*—RHS 68A and RHS 68B at the tip, the middle part is alternating RHS 62B and RHS 150D, the base is RHS 144D.

*Length.*—8.5-9.0 cm.

*Width.*—3.0 cm.

*Shape.*—Elongated, spindle shape.

Immature flower:

*Diameter.*—8.0 cm.

*Vertical diameter.*—About 8.0 cm.

*Color upper surface.*—RHS 65A overlain with RHS 68A.

*Color lower surface.*—RHS 68B with small irregular flecks of RHS 56D.

Mature flower:

*Shape.*—Funnelform, funnel shaped base, formed by 5 partly fused petals, with the petal lobes opening outwards, and a little overlapping.

*Flower, horizontal diameter.*—10.0-11.0 cm.

*Flower, vertical diameter.*—About 8.0 cm.

*Flower, diameter of the funnel.*—1.7 cm.

*Flower color, general.*—Light lavender pink, darker at petal apex and around throat opening.

*Flower color, upper surface.*—RHS 65A overlain with RHS 68B.

*Flower color, lower surface.*—RHS 68B with small irregular flecks of RHS 56D.

*Color of the funnel, inner side.*—RHS 16A.

*Color of the funnel, outside.*—RHS 62B with lighter tones.

*Petal, shape.*—Roughly ovate, asymmetric.

*Petal apex shape.*—Mucronate.

*Petal base shape.*—Fused.

*Petal margin.*—Mainly entire.

*Petal length, from the corolla opening.*—5.0 cm.

*Petal width, maximum.*—4.3 cm.

*Corolla, texture of upper surface.*—Glabrous, papillose.

*Corolla, texture of lower surface.*—Glabrous, papillose.

*Pedicel, color.*—Light green, RHS 146D.
*Length.*—2.0 cm.
*Diameter.*—0.20 cm.
*Pedicel, texture.*—Smooth, glabrous.

Calyx:
*Form.*—5 sepals, closely attached to the base of the flower.
*Color, visible outer surface.*—RHS 145B.
*Length.*—1.2 cm.
*Width.*—0.45 cm.
*Shape.*—Subulate.
*Apex shape.*—Acute.
*Base.*—Fused.
*Margins.*—Entire.
*Texture, upper surface.*—Glabrous.

Reproductive organs:

Gynoecium:
*Pistil.*—1, with a 5-lobed stigma.
*Style length.*—2.5 cm.
*Diameter.*—0.05 cm.
*Style color.*—RHS 150D.
*Stigma color.*—RHS 185B and RHS 145B.
*Stigma shape.*—Five lobed.
*Ovary color.*—RHS 144B.

Androecium:
*Stamens.*—5, connivent, surrounding the style and stigma.
*Filaments.*—Fused with the base of the flower.
*Anther.*—Elongated.
*Anther color.*—RHS 164D.
*Anther length.*—1.2 cm.
*Color of pollen.*—RHS 4D.
*Pollen amount.*—Moderate.

Fertility/seed set: Has not been observed on this hybrid.

Disease/pest resistance: Has not been observed on this hybrid.

What is claimed is:

1. A new and distinct variety of *Mandevilla* plant named 'MANZ0003' substantially as illustrated and described herein.

* * * * *